(12) United States Patent
Cheong et al.

(10) Patent No.: US 7,759,511 B2
(45) Date of Patent: Jul. 20, 2010

(54) LIQUID CRYSTAL COMPOSITION COMPRISING NOVEL SILICON CONTAINING COMPOUNDS AND LIQUID CRYSTAL DISPLAY DEVICE USING THE SAME

(75) Inventors: Jae Ho Cheong, Daejeon (KR); Min Jin Ko, Daejeon (KR); Dae Ho Kang, Daejeon (KR); Ki Youl Lee, Daejeon (KR); Youn Bong Kim, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/330,171

(22) Filed: Jan. 12, 2006

(65) Prior Publication Data

US 2006/0151744 A1 Jul. 13, 2006

(30) Foreign Application Priority Data

Jan. 13, 2005 (KR) .................... 10-2005-0003159

(51) Int. Cl.
*C07F 7/04* (2006.01)
(52) U.S. Cl. .................................................... 556/431
(58) Field of Classification Search ............ 252/299.62; 349/182; 546/14; 556/431
See application file for complete search history.

(56) References Cited

U.S. PATENT DOCUMENTS

| | | | |
|---|---|---|---|
| 4,730,904 A | | 3/1988 | Pauluth et al. |
| 4,864,027 A | * | 9/1989 | Shubert et al. ................. 546/14 |
| 5,399,290 A | | 3/1995 | Häberle et al. |
| 5,498,368 A | | 3/1996 | Coles |
| 5,690,858 A | * | 11/1997 | Nohira et al. ........... 252/299.01 |
| 5,840,288 A | * | 11/1998 | Guskey et al. ................. 424/65 |
| 5,942,155 A | * | 8/1999 | Coles et al. ............ 252/299.64 |
| 2001/0038091 A1 | | 11/2001 | Yanai et al. |

FOREIGN PATENT DOCUMENTS

| | | |
|---|---|---|
| DE | 102 22 509 | 3/2003 |
| EP | 1 160 250 | 12/2001 |
| JP | 10-114894 | 5/1998 |
| JP | 11-029580 | 2/1999 |
| JP | 11-061133 | 3/1999 |
| JP | 2002-255974 | 9/2002 |
| KR | 10-2003-0074467 | 9/2003 |
| KR | 10-2006-0082820 | 7/2006 |
| TW | 296384 | 1/1997 |
| TW | 546301 | 8/2003 |
| WO | WO 03/040812 | 5/2003 |

OTHER PUBLICATIONS

Yoda et al., Multiphase emulsions by liquid crystal emulsification and their application, Shikizai Kyokaishi (2004), 77(7), 309-313.*

* cited by examiner

*Primary Examiner*—Sikarl A Witherspoon
*Assistant Examiner*—Chukwuma O Nwaonicha
(74) *Attorney, Agent, or Firm*—McKenna Long & Aldridge LLP

(57) ABSTRACT

Disclosed are a silicon-containing compound, a liquid crystal composition comprising the same compound, and a liquid crystal display device comprising a liquid crystal layer prepared from the liquid crystal composition. The silicon-containing compound, which forms the liquid crystal composition, has low viscosity and high positive dielectric anisotropy. Therefore, it is possible to provide a liquid crystal display device, which has a fast response time and can be driven at a low voltage.

6 Claims, No Drawings

LIQUID CRYSTAL COMPOSITION COMPRISING NOVEL SILICON CONTAINING COMPOUNDS AND LIQUID CRYSTAL DISPLAY DEVICE USING THE SAME

This application claims the benefit of the filing date of Korean Patent Application No. 10-2005-0003159, filed on Jan. 13, 2005, in the Korean Intellectual Property Office, the disclosure of which is incorporated herein in its entirely by reference.

TECHNICAL FIELD

The present invention relates to a novel silicon-containing compound and a liquid crystal composition comprising the same. More particularly, the present invention relates to a novel nematic liquid crystal compound, which has low viscosity and high positive dielectric anisotropy, a liquid crystal composition comprising the same compound, and a liquid crystal display device using the same composition.

BACKGROUND ART

In general, liquid crystal compounds having optical anisotropy ($\Delta n$) and dielectric anisotropy ($\Delta \in$) are widely used in display devices such as clocks, notebook PCs, mobile phones, televisions and monitors. Such liquid crystal compounds are increasingly in demand. Liquid crystal compounds used in such display devices include a nematic liquid crystal phase, a smectic liquid crystal phase and a cholesteric liquid crystal phase. Among those phases, nematic phases are the most widely used. In practice, various liquid crystal compounds are used in the form of a composition. Liquid crystal compositions should be stable against water, light, heat, air, electric fields or the like, and have to ensure the chemical stability among the compounds forming the composition under the conditions of particular use. In order to use a liquid crystal compound in a display device, the liquid crystal compound should be in harmony of physical properties, including a wide range of liquid crystal phase temperatures, optical anisotropy value ($\Delta n$) and dielectric anisotropy value ($\Delta \in$), viscosity and conductivity. Properties of a liquid crystal compound required for a display device depend on the specific type of the display device. Therefore, there is an imminent need for a novel liquid crystal device that satisfies the above properties at the same time. Recently, there has been a need for a liquid crystal display device having a fast response time in order to treat a great amount of information promptly.

DISCLOSURE OF THE INVENTION

Therefore, the present invention has been made in view of the above-mentioned problems. It is an object of the present invention to provide a novel liquid crystal compound, which has low viscosity as well as high positive dielectric anisotropy so as to permit optimization of display. It is another object of the present invention to provide a liquid crystal composition comprising the above compound. It is still another object of the present invention to provide a liquid crystal display device manufactured by using the above composition.

The present invention provides a novel silicon-containing compound represented by the following formula 1, a liquid crystal composition comprising the above compound, and a liquid crystal display device comprising a liquid crystal layer prepared from the above liquid crystal composition:

[Formula 1]

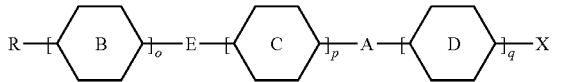

(I)

wherein A is selected from the group consisting of $SiMe_2O_{k1}(CQ_2)_{n1}$, $SiEt_2O_{k1}(CQ_2)_{n1}$, $SiF_2O_{k1}(CQ_2)_{n1}$, $SiCl_2O_{k1}(CQ_2)_{n1}$, $SiMe_2(CQ_2)_{n1}O_{k1}$, $SiEt_2(CQ_2)_{n1}O_{k1}$, $SiF_2(CQ_2)_{n1}O_{k1}$, $SiCl_2(CQ_2)_{n1}O_{k1}$, $O_{k1}SiMe_2(CQ_2)_{n1}$, $O_{k1}SiEt_2(CQ_2)_{n1}$, $O_{k1}SiF_2(CQ_2)_{n1}$, $O_{k1}SiCl_2(CQ_2)_{n1}$, $(CQ_2)_{n1}O_{k1}SiMe_2$, $(CQ_2)_{n1}O_{k1}SiEt_2$, $(CQ_2)_{n1}O_{k1}SiF_2$, $(CQ_2)_{n1}O_{k1}SiCl_2$, $O_{k1}(CQ_2)_{n1}SiMe_2$, $O_{k1}(CQ_2)_{n1}SiEt_2$, $O_{k1}(CQ_2)_{n1}SiF_2$, $O_{k1}(CQ_2)_{n1}SiCl_2$, $(CQ_2)_{n1}SiMe_2O_{k1}$, $(CQ_2)_{n1}SiEt_2O_{k1}$, $(CQ_2)_{n1}SiF_2O_{k1}$, $(CQ_2)_{n1}SiCl_2O_{k1}$, $(CH_2)_{n1}$, $CH=CH$, $C\equiv C$, O, S, COO, OCO, $CF_2O$, $OCF_2$, OCOO, $CH_2O$, $CH_2CO$, $OCH_2$ and $COCH_2$, wherein $k_1$ is 0 or 1, Q is H or F, $n_1$ is an integer between 0 and 3;

ring B is selected from the group consisting of

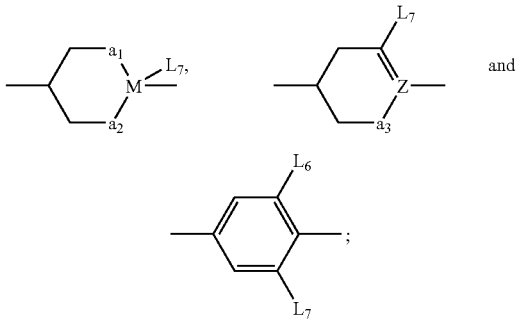

ring C is selected from the group consisting of

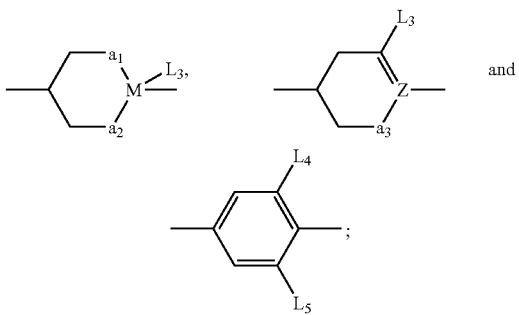

ring D is selected from the group consisting of

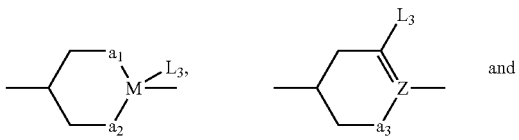

-continued

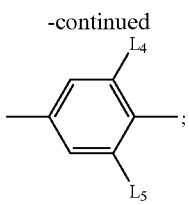

wherein the substituents, which are introduced into ring B, ring C or ring D and represented by $L_1$ to $L_7$, are independent from each other, even if they have the same designations;

M is selected from C, N and Si, with the proviso that if M is N, $L_3$ or $L_7$ is null;

Z is C;

each of $a_1$, $a_2$ and $a_3$ is independently selected from C, NR and O;

E is selected from the group consisting of $SiMe_2O_{k2}(CQ_2)_{n2}$, $SiEt_2O_{k2}(CQ_2)_{n2}$, $SiF_2O_{k2}(CQ_2)_{n2}$, $SiCl_2O_{k2}(CQ_2)_{n2}$, $SiMe_2(CQ_2)_{n2}O_{k2}$, $SiEt_2(CQ_2)_{n2}O_{k2}$, $SiF_2(CQ_2)_{n2}O_{k2}$, $SiCl_2(CQ_2)_{n2}O_{k2}$, $O_{k2}SiMe_2(CQ_2)_{n2}$, $O_{k2}SiEt_2(CQ_2)_{n2}$, $O_{k2}SiF_2(CQ_2)_{n2}$, $O_{k2}SiCl_2(CQ_2)_{n2}$, $(CQ_2)_{n2}O_{k2}SiMe_2$, $(CQ_2)_{n2}O_{k2}SiEt_2$, $(CQ_2)_{n2}O_{k2}SiF_2$, $(CQ_2)_{n2}O_{k2}SiCl_2$, $O_{k2}(CQ_2)_{n2}SiMe_2$, $O_{k2}(CQ_2)_{n2}SiEt_2$, $O_{k2}(CQ_2)_{n2}SiF_2$, $O_{k2}(CQ_2)_{n2}SiCl_2$, $(CQ_2)_{n2}SiMe_2O_{k2}$, $(CQ_2)_{n2}SiEt_2O_{k2}$, $(CQ_2)_{n2}SiF_2O_{k2}$, $(CQ_2)_{n2}SiCl_2O_{k2}$, $(CH_2)_{n2}$, C≡C, O, S, COO, OCO, $CF_2O$, $OCF_2$, OCOO, $CH_2O$, $CH_2CO$, $OCH_2$ and $COCH_2$, wherein $k_2$ is 0 or 1, Q is H or F, and $n_2$ is an integer between 0 and 3;

R is selected from the group consisting of H, a $C_1$~$C_{15}$ alkyl group, a $C_2$~$C_{15}$ alkene group and an alkoxy group ($R_1O$), wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E,Z), $CH_2CH_2CH=CHCH_3$ (E,Z) or $CH_2CH_2CH_2CH=CH_2$;

$R_1$ is selected from the group consisting of H, a $C_1$~$C_{15}$ alkyl group and a $C_2$~$C_{15}$ alkene group, wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E,Z), $CH_2CH_2CH=CHCH_3$ (E,Z) or $CH_2CH_2CH_2CH=CH_2$;

X is selected from the group consisting of H, $SiR_2R_3R_4$, $CF_3$, $OCF_3$, CN, NCS, halogen atoms and R;

each of $R_2$, $R_3$ and $R_4$ is independently selected from R and halogen atoms;

each of $L_1$, $L_2$, $L_3$, $L_4$, $L_5$, $L_6$ and $L_7$ is independently selected from the group consisting of H, halogen atoms, CN, $CF_3$, $OCF_3$ and NCS;

each of o, p and q independently represents an integer between 0 and 2; and at least one of E, A and X contains silicon.

Hereinafter, the present invention will be explained in more detail.

The present invention provides a novel silicon-containing compound that may be applied in various display devices, a liquid crystal composition essentially comprising the silicon-containing compound, preferably a positive nematic liquid crystal composition, and a liquid crystal display device using the above liquid crystal composition. The silicon-containing compound is characterized by having low viscosity, and zero (0) or high positive (+) dielectric anisotropy.

High dielectric anisotropy is required for the operation of a liquid crystal under a low driving voltage. According to the present invention, the liquid crystal compound has symmetry of substituents based on the major axis of the molecule, thereby providing high positive dielectric anisotropy.

Low viscosity is required to obtain a fast response time of a liquid crystal. According to the compound of the present invention, it is possible to obtain low viscosity by introducing a silicon-containing substituent into at least one of the linking groups (A and E) and terminal group (X), or both of the linking groups and terminal group.

Further, according to the present invention, it is possible to improve dipole moment by introducing a halogen atom and/or alkyl group as a substituent for the hydrogen atom, which forms a primary bond with silicon when a silicon-containing substituent is introduced into at least one of the linking groups and/or terminal group. Such improved dipole moment results in improvement in the dielectric anisotropy, which is affected significantly by the polarizability and dipole moment.

Preferred embodiments of the silicon-containing compound represented by formula 1 according to the present invention, which comprise preferred examples of ring B and ring C, are represented by the following formulae 2~10. However, the scope of the present invention is not limited thereto.

[Formula 2]

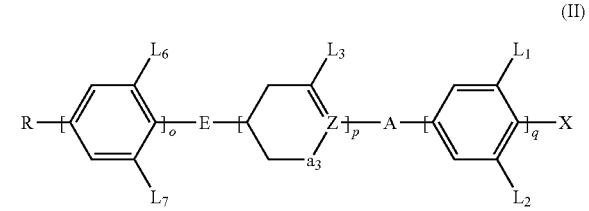

(II)

[Formula 3]

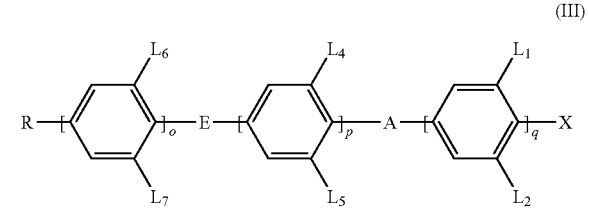

(III)

[Formula 4]

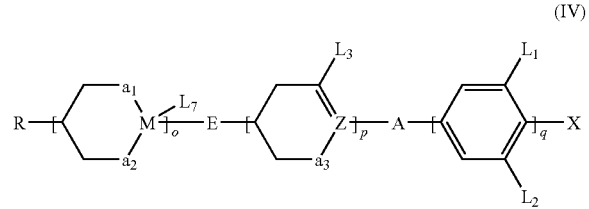

(IV)

[Formula 5]

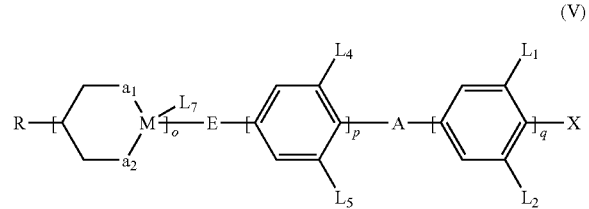

(V)

-continued

[Formula 6]

(VI)
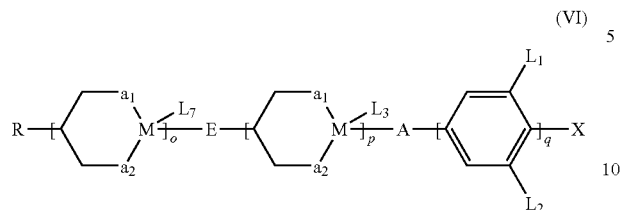

[Formula 7]

(VII)
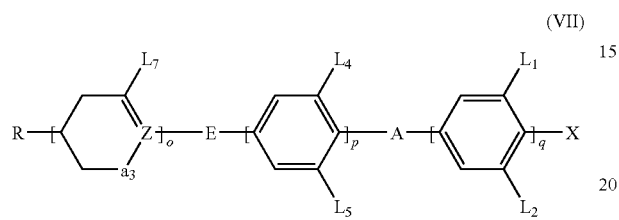

[Formula 8]

(VIII)
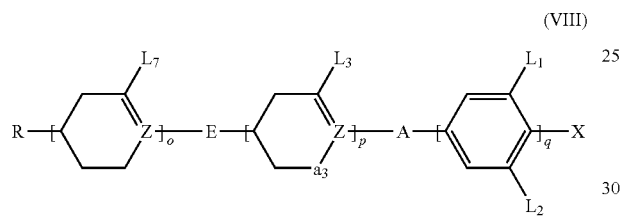

[Formula 9]

(IX)
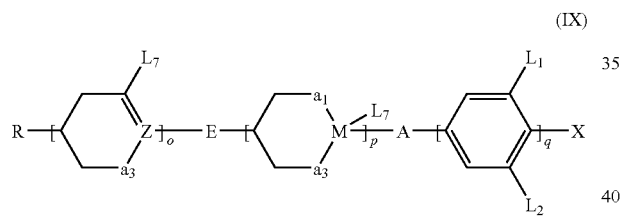

[Formula 10]

(X)
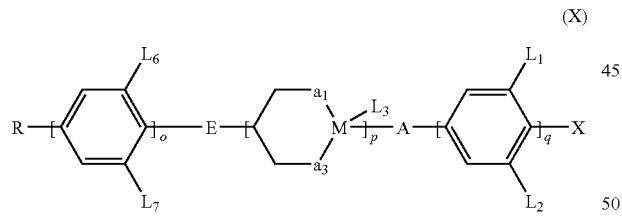

wherein Z is C;

M is C, N or Si, with the proviso that if M is N, $L_3$ or $L_7$ is null;

each of $a_1$, $a_2$ and $a_3$ is independently selected from C, NR and O;

each of $L_1$, $L_2$, $L_3$, $L_4$, $L_5$, $L_6$ and $L_7$ is independently selected from the group consisting of H, halogen atoms, CN, $CF_3$, $OCF_3$ and NCS; and A, E, R, X, o, p and q are the same as defined in formula 1.

Particular preferred examples of the compounds represented by formulae 2~10 include the following compounds. However, the scope of the present invention is not limited thereto.

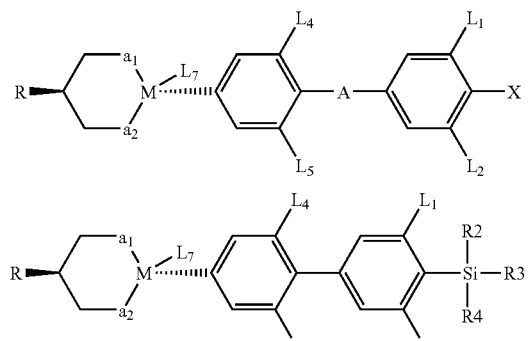

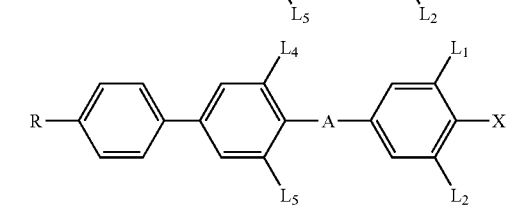

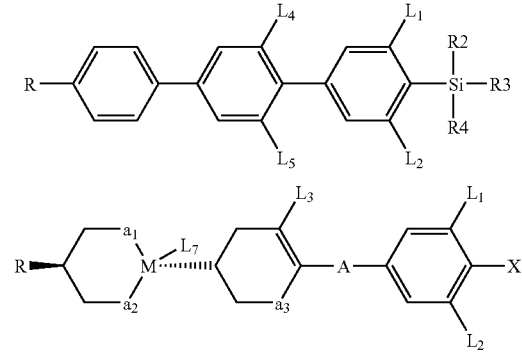

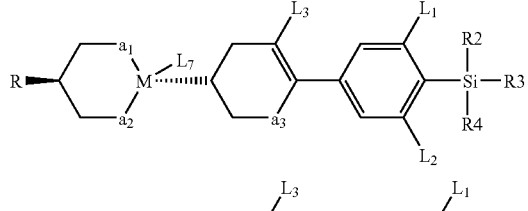

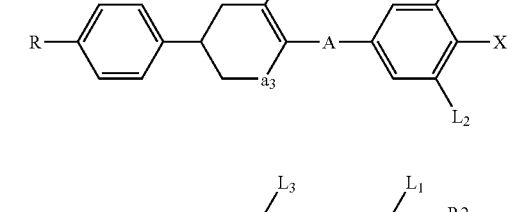

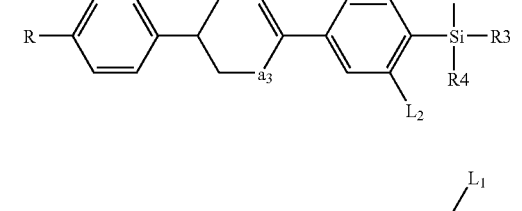

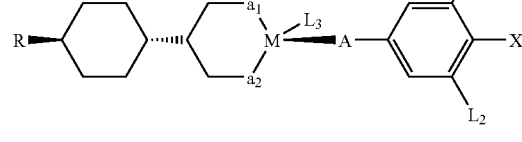

-continued

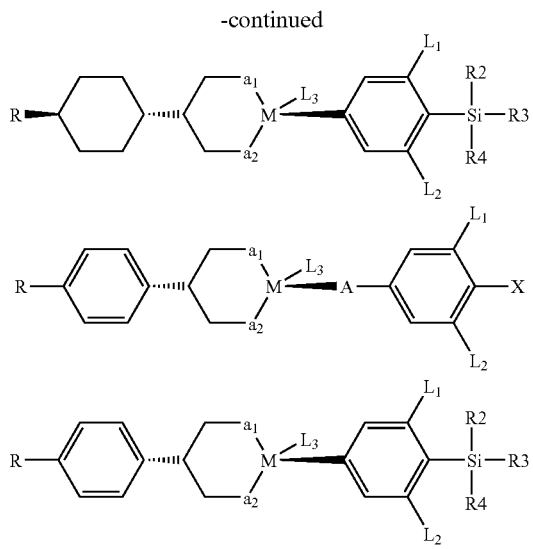

wherein A is selected from the group consisting of $SiO_{k1}$ $(CQ_2)_{n1}$, $Si(CQ_2)_{n1}O_{k1}$, $(CQ_2)_{n1}O_{k1}Si$, $(CQ_2)_{n1}SiO_{k1}$, $O_{k1}$ $(CQ_2)_{n1}Si$ and $O_{k1}Si(CQ_2)_{n1}$, and $k_1$, Q, $n_1$, R, $R_2$, $R_3$, $R_4$, $L_1$, $L_2$, $L_3$, $L_4$, $L_5$, $L_7$, X, M, $a_1$, $a_2$ and $a_3$ are the same as defined in formula 1.

Stereoisomers of the silicon-containing compound represented by formula 1 are also included in the scope of the present invention. Herein, the silicon-containing compound having stereoisomers is present preferably in the trans-form with liquid crystal characteristics. Additionally, stereoisomers of the silicon-containing compound may be present in the ratio of trans-isomer:cis-isomer of 85~100:15~0, but are not limited thereto.

The novel silicon-containing compound represented by formula 1 is chemically and thermally stable, is stable to light, and can form a mesomorphic phase (meso-phase) at a desired temperature range so as to be used suitably for display applications.

The silicon-containing compound represented by formula 1 according to the present invention may be prepared by a method generally known to one skilled in the art. According to a preferred embodiment of the present invention, the silicon-containing compound represented by formula 1 may be prepared by way of the following Reaction Schemes 1~5.

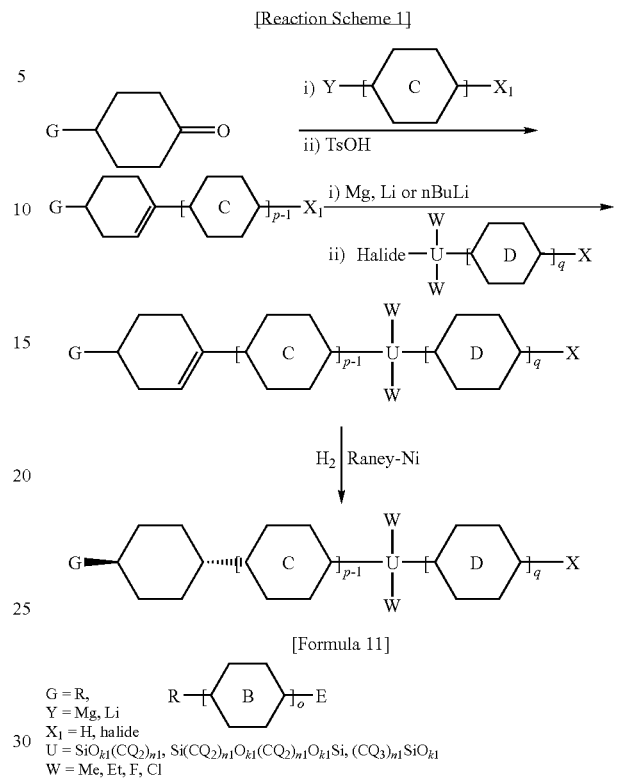

[Formula 11]

G = R,   R—(B)$_o$—E
Y = Mg, Li
$X_1$ = H, halide
U = $SiO_{k1}(CQ_2)_{n1}$, $Si(CQ_2)_{n1}O_{k1}(CQ_2)_{n1}O_{k1}Si$, $(CQ_3)_{n1}SiO_{k1}$
W = Me, Et, F, Cl In one embodiment of the method represented by Reaction Scheme 1, a Grignard reagent is formed from 1,4-dibromobenzene with Mg, followed by a reaction with 4-n-propylcyclohexane and dehydration using TsOH. The resultant product is allowed to react with n-BuLi to form an anion, which in turn is allowed to react with a silyl chloride derivative. Next, hydrogenation is performed by using the Raney-Nickel catalyst in order to form a trans isomer, thereby providing a silyl liquid crystal compound represented by formula 11. Otherwise, the trans isomer may be formed by way of hydrogenation using Pd/charcoal and recrystallization. Herein, the silyl chloride derivative may be formed according to a method generally known to one skilled in the art. For example, Mg is added to 1-bromo-4-fluorobenzene to form a Grignard reagent, and an excessive amount of $Me_2SiCl_2$ is added thereto to provide the silyl chloride derivative.

[Reaction Scheme 2]

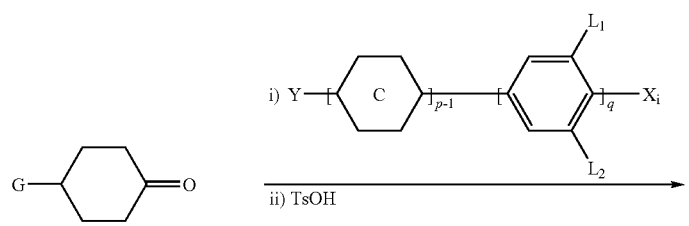

-continued

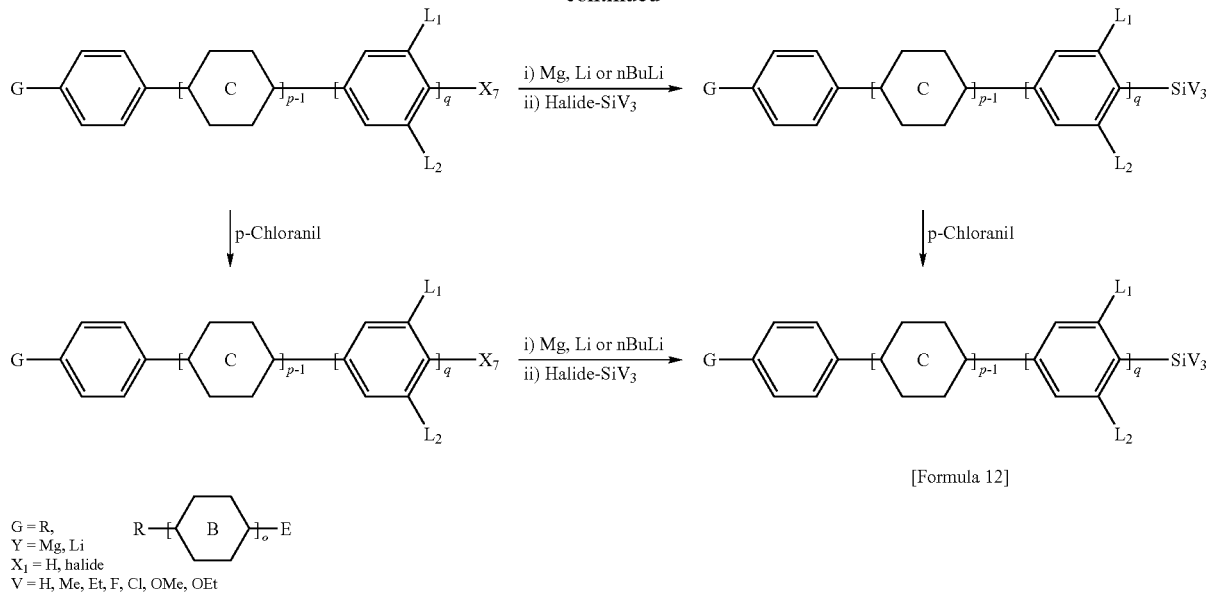

[Formula 12]

In one embodiment of the method represented by Reaction Scheme 2, 4,4'-dibromobiphenyl is subjected to the Grignard reaction, followed by dehydration using TsOH. Then, the resultant product is converted into an anionic form with n-BuLi, and then is allowed to react with the silyl chloride derivative. If the reaction with p-chloranil is used instead of hydrogenation, the silyl liquid crystal compound represented by formula 12 can be obtained.

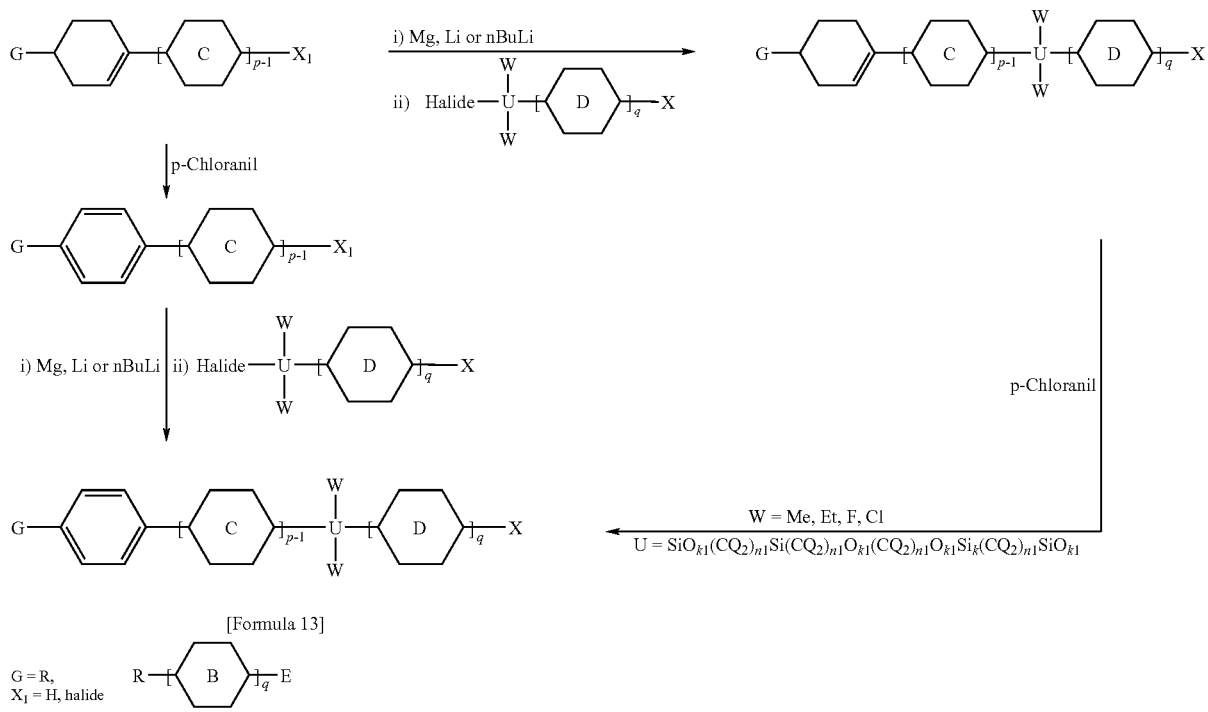

[Formula 13]

In one embodiment of the method represented by Reaction Scheme 3, 1,4-dibromobenzene and 4-n-propylcyclohexanone are subjected to a coupling reaction in the presence of Mg to provide a tertiary alcohol, followed by dehydration using TsOH, thereby providing the starting material. Next, the starting material is converted into a Grignard reagent by using Mg, and the Grignard reagent is allowed to react with the silyl chloride derivative. Then, the resultant product is allowed to react with p-chloranil to provide the silyl liquid crystal compound represented by formula 13.

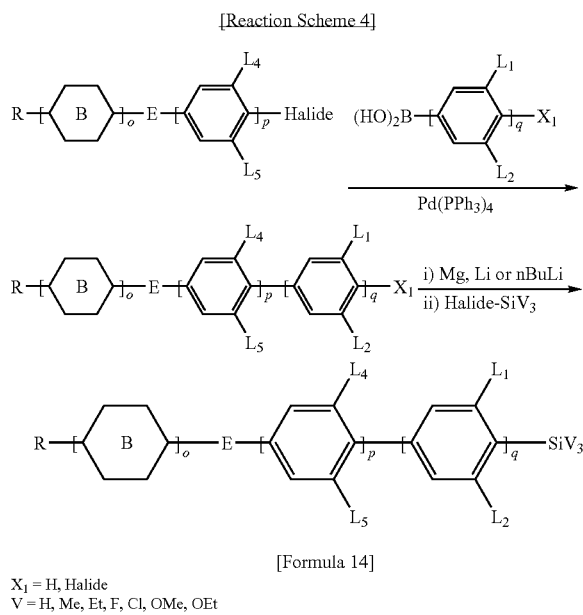

[Formula 14]

$X_1$ = H, Halide
V = H, Me, Et, F, Cl, OMe, OEt

In one embodiment of the method represented by Reaction Scheme 4, phenylboronic acid is added to 4-bromo-4'-propylbiphenyl and the reaction mixture is subjected to a coupling reaction in the presence of $Pd(PPh_3)_4$ to provide the triphenyl compound. Then, a silyl group is introduced to the triphenyl compound by using magnesium or alkyllithium to provide the silyl liquid crystal compound represented by formula 14.

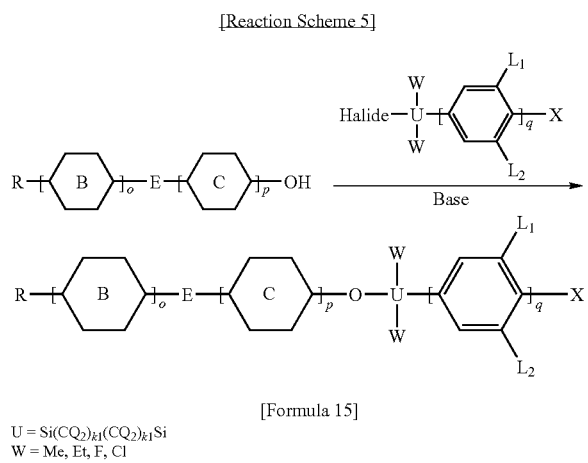

[Formula 15]

U = $Si(CQ_2)_{k1}(CQ_2)_{k1}Si$
W = Me, Et, F, Cl

In one embodiment of the method represented by Reaction Scheme 5, trans,trans-4-(4-propylcyclohexyl) cyclohexan-1-ol and chlorodimethylphenylsilane are dissolved in a dry solvent, and the reaction mixture is allowed to react at room temperature in the presence of a base added thereto to provide the liquid crystal compound containing a —O—Si— bond, represented by formula 15.

In addition to the compounds obtained by way of the above Reaction Schemes 1~5, compounds obtained by similar methods or conventional methods known to one skilled in the art are also included in the scope of the present invention. The silicon-containing compounds obtained as described above may be mixed in an adequate ratio to provide a liquid crystal composition.

The present invention provides a liquid crystal composition, preferably a nematic liquid crystal composition, which comprises the silicon-containing compound represented by formula 1.

To provide the desired liquid crystal characteristics by a liquid crystal composition, about 5~20 components are generally used in combination in the liquid crystal composition. According to the present invention, it is possible to provide a liquid crystal composition having a low driving voltage and a fast response time by using the novel silicon-containing compound represented by formula 1, which can serve to impart high positive dielectric anisotropy as well as to reduce viscosity.

Although there is no particular limitation in the content of the compound represented by formula 1, more particularly at least one compound selected from the group consisting of the silicon-containing liquid crystal compounds represented by formulae 2~10, each compound is preferably used in an amount of 1~50 wt % based on 100 wt % of the total liquid crystal composition.

The liquid crystal composition according to the present invention may further comprise other liquid crystal compounds, currently used in a conventional liquid crystal composition, in addition to the silicon-containing compound represented by formula 1. Such compounds may be used in a controlled ratio, as necessary. Additionally, suitable additives may also be used, and such additives are disclosed in [H. Kelker/R. Hatz, Handbook of Liquid Crystals, Verlag Chemie, Weinheim, 1980]. For example, additives for modifying the dielectric anisotropy, viscosity and/or alignment of a nematic phase may be used. Particular examples of the additives that may be used in the liquid crystal composition according to the present invention include chiral dopants that inhibit the helical structure and reverse distortion of a liquid crystal, dichroic dyes, or the like.

The liquid crystal composition according to the present invention may be prepared by a method generally known to one skilled in the art. In one embodiment of such methods, various components that form the liquid crystal composition are dissolved at a temperature ranging from room temperature to a high temperature.

Also, the present invention provides a liquid display device, which comprises a liquid crystal layer obtained from the liquid crystal composition.

There is no particular limitation in the liquid crystal display device. Particular examples of the liquid crystal display device include a simple matrix type twist nematic liquid crystal display device, simple matrix type supertwist nematic liquid crystal display device, active matrix type TFT (thin film transistor) liquid crystal display device, active matrix type MIM (metal insulator metal) liquid crystal display device, active matrix type IPS (in-plane switching) liquid crystal device, or the like.

The liquid crystal display device according to the present invention may be manufactured by a method generally known to one skilled in the art. One embodiment of such methods, a liquid crystal composition is dissolved at a suitable temperature, and then introduced into a liquid crystal device. The liquid crystal phase, dissolved as mentioned above, may be modified so that it can be applied for all types of liquid crystal display devices by virtue of the use of suitable additives.

BEST MODE FOR CARRYING OUT THE INVENTION

Reference will now be made in detail to the preferred embodiments of the present invention. It is to be understood that the following examples are illustrative only and the present invention is not limited thereto.

EXAMPLES 1~17

Example 1

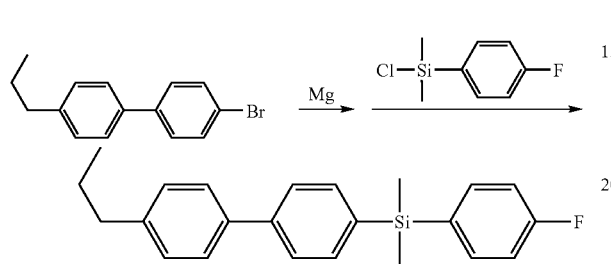

First, 25 ml of dichlorodimetylsilane was added to 50 ml of dry THF, and 100 ml of 1.0M 4-fluorophenylmagnesium bromide was added very slowly dropwise thereto. After the completion of the addition, the reaction mixture was stirred at low temperature for about 3 hours. Next, an excessive amount of hexane was added to the reaction mixture in order to precipitate a magnesium salt. The magnesium salt was removed via filtration and the organic solvent was evaporated completely under reduced pressure. Then, chlorodimethyl(4-fluorophenyl)silane was separated off via vacuum distillation (70~75° C./8 mPa). In a separate container, 255 mg of Mg was dissolved in 10 ml of dry THF. Next, a solution containing 2.88 g of 4-bromo-4'-n-propylbiphenyl dissolved in 20 ml of dry THF was added thereto to form a Grignard reagent, to which 1.97 g of chlorodimethyl(4-fluorophenyl)silane was added at room temperature. After stirring for about 10 hours, the reaction mixture was worked up with water and hexane, and then purified by silica gel column chromatography to obtain the silicon-containing compound represented by the above formula (yield: 88%). 400 MHz $^1$H-NMR, CDCl$_3$, δ (ppm): 0.57 (s, 6H), 0.99 (t, 3H), 1.65~1.69 (m, 2H), 2.64 (t, 2H), 7.07 (t, 2H), 7.25 (d, 2H), 7.54 (d, 2H), 7.58~7.61 (m, 6H).

Example 2

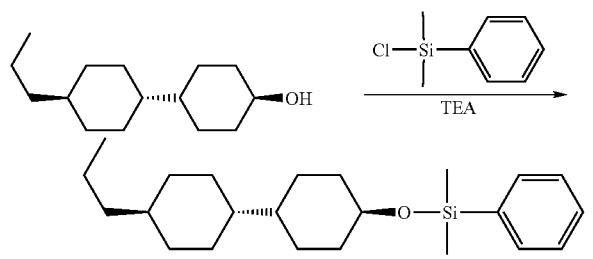

First, 2.0 g of trans, trans-cyclohexanol was dissolved in 20 ml of CH$_2$Cl$_2$, and 1.7 g of chlorodimethylphenylsilane and 1.08 g of triethylamine was added thereto at room temperature. After stirred for about 10 hours, the reaction mixture was worked up with water and CH$_2$Cl$_2$, and then purified by silica gel column chromatography to obtain the silicon-containing compound represented by the above formula (yield: 78%). 400 MHz $^1$H-NMR, CDCl$_3$, δ (ppm): 0.38 (s, 6H), 0.86~0.90 (m, 2H), 0.91 (t, 3H), 0.93~1.09 (m, 6H), 1.09~1.20 (m, 3H), 1.25~1.38 (m, 4H), 1.63~1.71 (br, 4H), 1.71~1.76 (br, 2H), 1.81~1.90 (br, 2H), 3.51 (m, 1H), 7.36~7.40 (m, 3H), 7.59~7.62 (m, 2H).

Example 3

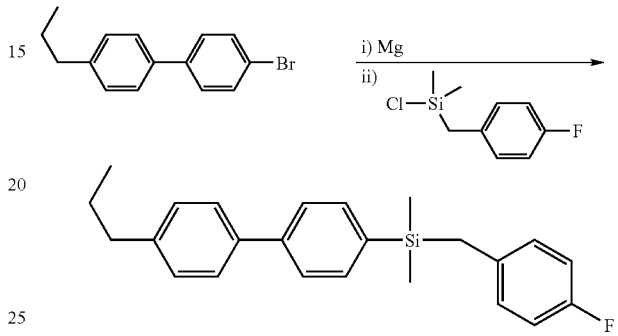

First, 6.45 g of dichlorodimethylsilane was dissolved in dry THF and cooled to 0° C. Next, 100 ml of 4-fluorobenzylmagnesium chloride (0.25 M) was slowly added dropwise thereto. After the completion of the addition, the reaction mixture was allowed to further react at low temperature for about 3 hours. Next, an excessive amount of hexane was added to the reaction mixture to precipitate a magnesium salt. The magnesium salt was removed via filtration and the organic solvent was evaporated under reduced pressure. By doing so, chlorodimethyl(4-fluorophenyl)silane was obtained with a yield of 80% via vacuum distillation. In a separate container, 3.0 g of 4-bromo-4'-n-propylbiphenyl and 250 mg of Mg was added to 20 ml of dry THF to provide a Grignard reagent, to which 2.3 g of chlorodimethyl(4-fluorophenyl)silane was added at room temperature. The reaction mixture was heated to 60° C. for about 10 hours, and worked up with water and hexane, and then purified by silica gel column chromatography to obtain the silicon-containing compound represented by the above formula (yield: 91%). 400 MHz $^1$H-NMR, CDCl$_3$, δ (ppm): 0.30 (s, 6H), 0.99 (t, 3H), 1.65~1.74 (m, 2H), 2.30 (s, 2H), 2.65 (t, 2H), 6.89 (d, 4H), 7.26~7.28 (m, 2H), 7.50 (d, 2H), 7.54 (d, 2H), 7.58 (d, 2H).

Example 4

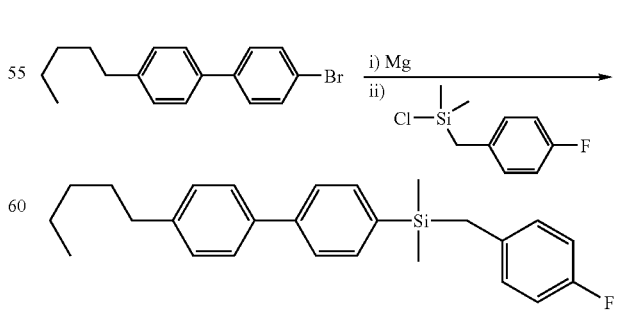

First, 3.03 g of 4-bromo-4'-n-pentylbiphenyl and 245 mg of Mg was introduced into 20 ml of dry THF to form a Grignard reagent, and then 2.05 g of chlorodimethyl(4-fluorobenzyl)silane was added thereto. The reaction mixture was heated to 60° C. for about 10 hours, and worked up with water and hexane, and then purified by silica gel column chromatography to obtain the silicon-containing compound represented by the above formula (yield: 94%). 400 MHz $^1$H-NMR, CDCl$_3$, δ (ppm): 0.31 (s, 6H), 0.91~0.97 (m, 3H), 1.36~1.45 (m, 4H), 1.65~1.77 (m, 2H), 2.33 (s, 2H), 2.69 (t, 2H), 6.91 (d, 4H), 7.27~7.32 (m, 2H), 7.53 (d, 2H), 7.56 (d, 2H), 7.61 (d, 2H).

Example 5

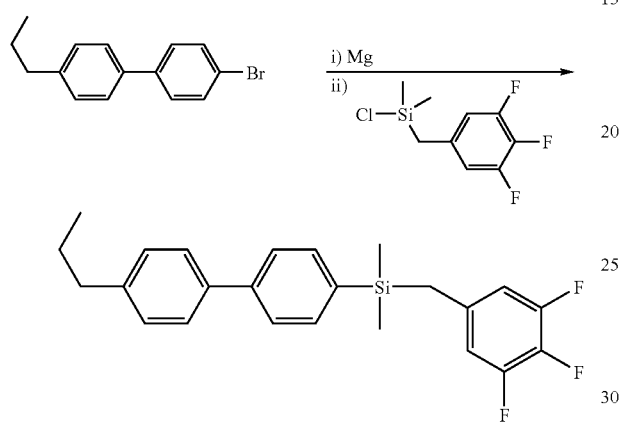

First, 6.45 g of dichlorodimethylsilane was dissolved in dry THF and cooled to 0° C. Next, 25 mmol of 3,4,5-trifluorobenzylmagnesium chloride was added slowly dropwise thereto. After the completion of the addition, the reaction mixture was allowed to further react at low temperature for about 3 hours. Next, an excessive amount of hexane was added to the reaction mixture to precipitate a magnesium salt. The magnesium salt was removed via filtration and the organic solvent was evaporated under reduced pressure. By doing so, chlorodimethyl(3,4,5-trifluorobenzylsilane) was obtained with a yield of 75% via vacuum distillation. In a separate container, 2.75 g of 4-bromo-4'-n-propylbiphenyl and 245 mg of Mg was added to 20 ml of dry THF to provide a Grignard reagent, to which 2.4 g of chlorodimethyl(3,4,5-trifluorobenzyl)silane was added at room temperature. The reaction mixture was heated to 60° C. for about 10 hours, and worked up with water and hexane, and then purified by silica gel column chromatography to obtain the silicon-containing compound represented by the above formula (yield: 87%). 400 MHz $^1$H-NMR, CDCl$_3$, δ (ppm): 0.31 (s, 6H), 0.99 (t, 3H), 1.63~1.76 (m, 2H), 2.26 (s, 2H), 2.64 (t, 2H), 6.46~6.54 (m, 2H), 7.26 (d, 2H), 7.48 (d, 2H), 7.53 (d, 2H), 7.59 (d, 2H).

Example 6

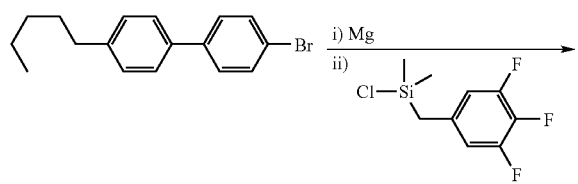

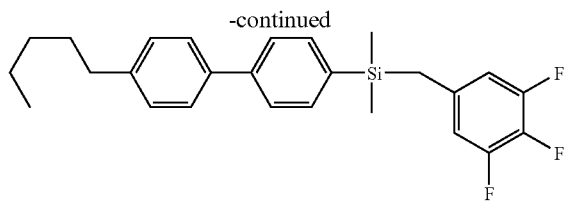

First, 3.03 g of 4-bromo-4'-n-pentylbiphenyl and 245 mg of Mg was introduced into 20 ml of dry THF to form a Grignard reagent, and then 2.4 g of chlorodimethyl(3,4,5-trifluorobenzyl)silane was added thereto. The reaction mixture was heated to 60° C. for about 10 hours, and worked up with water and hexane, and then purified by silica gel column chromatography to obtain the silicon-containing compound represented by the above formula (yield: 85%). 400 MHz $^1$H-NMR, CDCl$_3$, δ (ppm): 0.35 (s, 6H), 0.93~0.98 (m, 3H), 1.33~1.48 (m, 4H), 1.65~1.77 (m, 2H), 2.29 (s, 2H), 2.68 (t, 2H), 6.50~6.59 (m, 2H), 7.32 (d, 2H), 7.52 (d, 2H), 7.58 (d, 2H), 7.63 (d, 2H).

Example 7

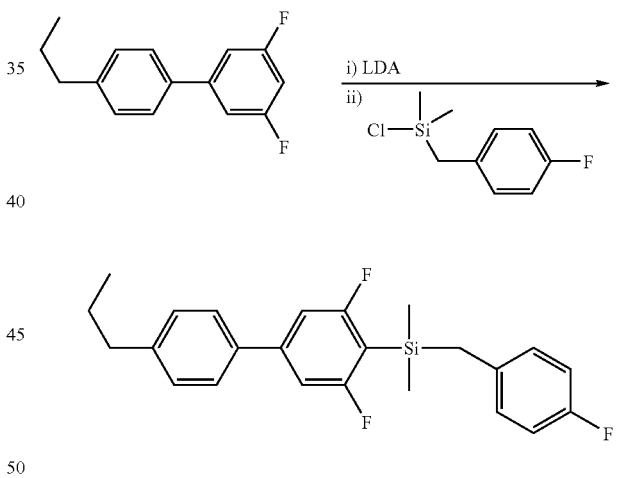

First, 2.32 g of 3,5-difluoro-4'-n-propylbiphenyl was added to 20 ml of dry THF, and 5 ml of 2.0M LDA was added dropwise thereto at −78° C. The reaction mixture was allowed to react sufficiently at low temperature for about 3 hours to form an anion. Next, 2.05 g of chlorodimethyl(4-fluorobenzyl)silane was added thereto, and the reaction mixture was warmed gradually to room temperature. After stirred at room temperature for about 1 hour, the reaction mixture was worked up with water and hexane, and then purified by silica gel column chromatography to obtain the silicon-containing compound represented by the above formula (yield: 90%). 400 MHz $^1$H-NMR, CDCl$_3$, δ (ppm): 0.35 (s, 6H), 0.98 (t, 3H), 1.64~1.74 (m, 2H), 2.43 (s, 2H), 2.65 (t, 2H), 6.87~6.97 (m, 4H), 7.05 (d, 2H), 7.28 (d, 2H), 7.50 (d, 2H).

Example 8

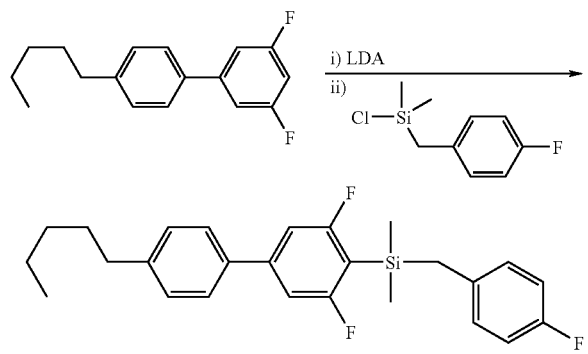

First, 2.60 g of 3,5-difluoro-4'-n-pentylbiphenyl was added to 20 ml of dry THF, and 5 ml of 2.0M LDA was added dropwise thereto at −78° C. The reaction mixture was allowed to react sufficiently at low temperature for about 3 hours to form an anion. Next, 2.05 g of chlorodimethyl(4-fluorobenzyl)silane were added thereto, and the reaction mixture was warmed gradually to room temperature. After stirred at room temperature for about 1 hour, the reaction mixture was worked up with water and hexane, and then purified by silica gel column chromatography to obtain the silicon-containing compound represented by the above formula (yield: 85%). 400 MHz $^1$H-NMR, CDCl$_3$, δ (ppm): 0.35 (s, 6H), 0.91~0.93 (m, 3H), 1.31~1.43 (m, 4H), 1.60~1.73 (m, 2H), 2.42 (s, 2H), 2.65 (t, 2H), 6.86~6.98 (m, 4H), 7.05 (d, 2H), 7.28 (d, 2H), 7.49 (d, 2H).

Example 9

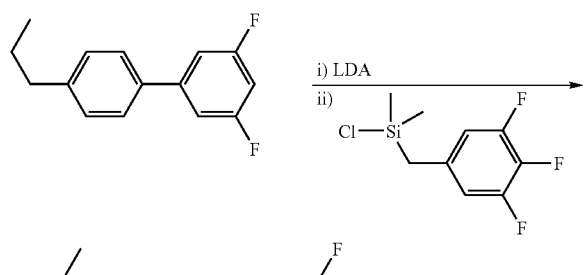

First, 2.32 g of 3,5-difluoro-4'-n-propylbiphenyl was added to 20 ml of dry THF, and 5 ml of 2.0M LDA was added dropwise thereto at −78° C. The reaction mixture was allowed to react sufficiently at low temperature for about 3 hours to form an anion. Next, 2.4 g of chlorodimethyl(3,4,5-trifluorobenzyl)silane were added thereto, and the reaction mixture was warmed gradually to room temperature. After stirred at room temperature for about 1 hour, the reaction mixture was worked up with water and hexane, and then purified by silica gel column chromatography to obtain the silicon-containing compound represented by the above formula (yield: 84%). 400 MHz $^1$H-NMR, CDCl$_3$, δ (ppm): 0.44 (s, 6H), 1.04 (t, 3H), 1.69~1.79 (m, 2H), 2.45 (s, 2H), 2.70 (t, 2H), 6.60~6.68 (m, 2H), 7.11 (d, 2H), 7.34 (d, 2H), 7.55 (d, 2H).

Example 10

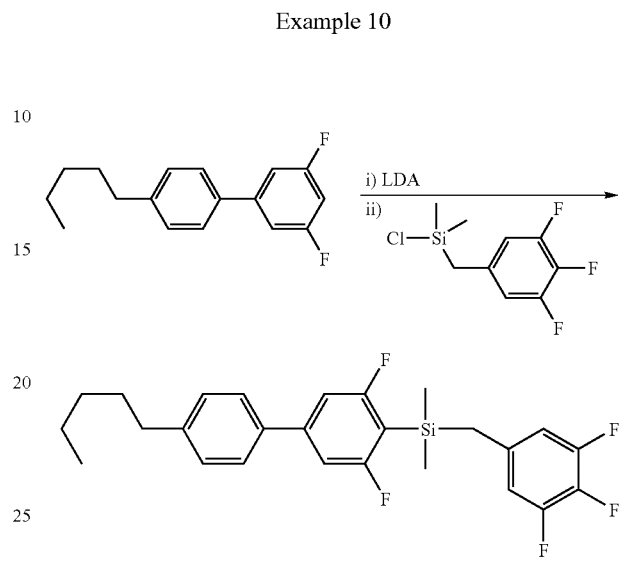

First, 2.6 g of 3,5-difluoro-4'-n-pentylbiphenyl was added to 20 ml of dry THF, and 5 ml of 2.0M LDA was added dropwise thereto at −78° C. The reaction mixture was allowed to react sufficiently at low temperature for about 3 hours to form an anion. Next, 2.4 g of chlorodimethyl(3,4,5-trifluorobenzyl)silane was added thereto, and the reaction mixture was warmed gradually to room temperature. After stirred at room temperature for about 1 hour, the reaction mixture was worked up with water and hexane, and then purified by silica gel column chromatography to obtain the silicon-containing compound represented by the above formula (yield: 80%). 400 MHz $^1$H-NMR, CDCl$_3$, δ (ppm): 0.40 (s, 6H), 0.85~0.96 (m, 3H), 1.31~1.42 (m, 4H), 1.61~1.72 (m, 2H), 2.40 (s, 2H), 2.64 (t, 2H), 6.55~6.62 (m, 2H), 7.05 (d, 2H), 7.28 (d, 2H), 7.49 (d, 2H)

Example 11

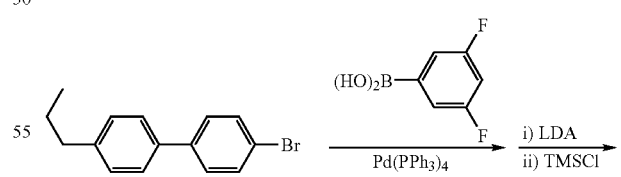

First, 3.0 g of 4-bromo-4'-n-propylbiphenyl was dissolved into 27 ml of DME as a solvent. Next, 2.05 g of 3,5-difluorophenylboronic acid, 380 mg of Pd(PPh$_3$)$_4$, and 27 ml of 2.0M Na$_2$CO$_3$ was added thereto. After refluxed at 100° C. for about 10 hours, the reaction mixture was worked up with water and hexane, and purified by silica gel column chromatography to obtain the triphenyl compound with a yield of 95%. Then, 3.0 g of the triphenyl compound was dissolved into 20 ml of dry THF and 5 ml of 2.0M LDA was slowly added dropwise thereto at −78° C. After an anion was formed over about 3 hours, 1.3 g of trimethylsilyl chloride was added to the anion at low temperature and the reaction mixture was warmed gradually to room temperature. After stirred at room temperature for about 1 hour, the reaction mixture was worked up with water and hexane, and then recrystallized from hexane/MeOH solvent to obtain the silicon-containing compound represented by the above formula (yield: 95%). 400 MHz $^1$H-NMR, CDCl$_3$, δ (ppm): 0.41 (s, 9H), 0.99 (t, 3H), 1.66~1.75 (m, 2H), 2.65 (t, 2H), 7.09 (d, 2H), 7.28 (d, 2H), 7.56 (d, 2H), 7.63 (d, 2H), 7.68 (d, 2H).

Example 12

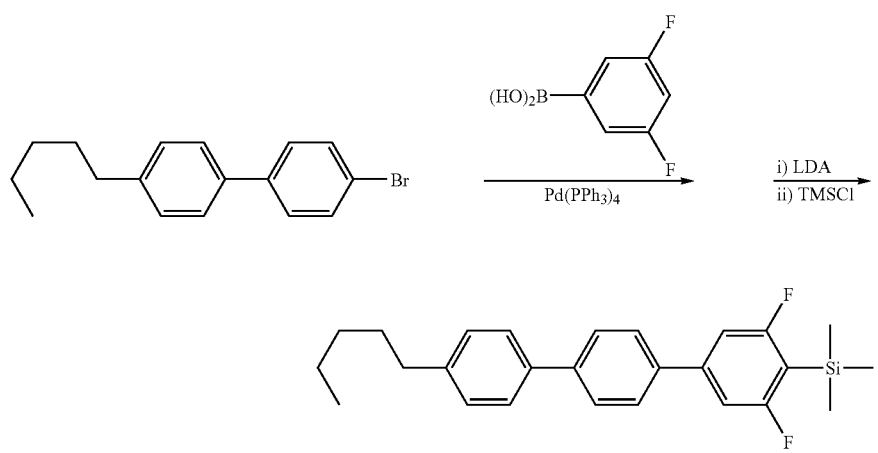

First, 3.3 g of 4-bromo-4'-n-pentylbiphenyl was dissolved into 27 ml of DME as a solvent. Next, 2.05 g of 3,5-difluorophenylboronic acid, 380 mg of Pd(PPh$_3$)$_4$ and 27 ml of 2.0M Na$_2$CO$_3$ was added thereto. After refluxed at 100° C. for about 10 hours, the reaction mixture was worked up with water and hexane, and then purified by silica gel column chromatography to obtain the triphenyl compound with a yield of 90%. Then, 3.0 g of the triphenyl compound was dissolved into 20 ml of dry THF and 4.5 ml of 2.0M LDA was slowly added dropwise thereto at −78° C. After an anion was formed over about 3 hours, 1.16 g of trimethylsilyl chloride was added to the anion at low temperature and the reaction mixture was warmed to room temperature. After stirred at room temperature for about 1 hour, the reaction mixture was worked up with water and hexane, and then recrystallized from hexane/MeOH solvent to obtain the silicon-containing compound represented by the above formula (yield: 92%). 400 MHz $^1$H-NMR, CDCl$_3$, δ (ppm): 0.41 (s, 9H), 0.87~0.95 (m, 3H), 1.31~1.42 (m, 4H), 1.63~1.72 (m, 2H), 2.67 (t, 2H), 7.09 (d, 2H), 7.28 (d, 2H), 7.56 (d, 2H), 7.63 (d, 2H), 7.68 (d, 2H).

Example 13

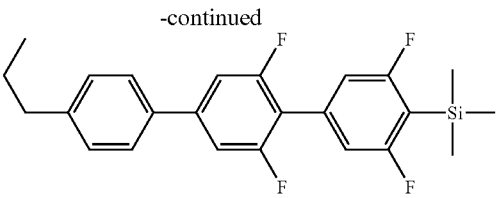

-continued

First, 3.9 g of 3,5-difluoro-4-iodo-4'-n-propylbiphenyl was dissolved into 27 ml of DME as a solvent. Next, 2.05 g of 3,5-difluorophenylboronic acid, 380 mg of Pd(PPh$_3$)$_4$ and 27 ml of 2.0M Na$_2$CO$_3$ was added thereto. After refluxed at 100° C. for about 10 hours, the reaction mixture was worked up with water and hexane, and then purified by silica gel column chromatography to obtain the triphenyl compound with a yield of 98%. Then, 3.4 g of the triphenyl compound was dissolved into 20 ml of dry THF and 5 ml of 2.0M LDA was slowly added dropwise thereto at −78° C. After an anion was formed over about 3 hours, 1.2 g of trimethylsilyl chloride was added to the anion at low temperature and the reaction mixture was warmed gradually to room temperature. After stirred at room temperature for about 1 hour, the reaction mixture was worked up with water and hexane, and then recrystallized from hexane/MeOH solvent to obtain the silicon-containing compound represented by the above formula (yield: 96%). 400 MHz $^1$H-NMR, CDCl$_3$, δ (ppm): 0.42 (s, 9H), 0.99 (t, 3H), 1.65~1.75 (m, 2H), 2.66 (t, 2H), 7.00 (d, 2H), 7.23 (d, 2H), 7.30 (d, 2H), 7.52 (d, 2H).

Example 14

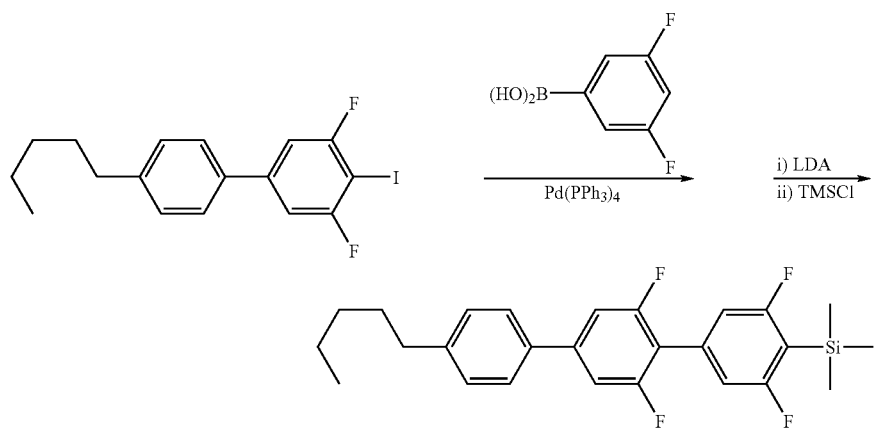

First, 4.2 g of 3,5-difluoro-4-iodo-4'-n-pentylbiphenyl was dissolved into 27 ml of DME as a solvent. Next, 2.05 g of 3,5-difluorophenylboronic acid, 380 mg of Pd(PPh$_3$)$_4$ and 27 ml of 2.0M Na$_2$CO$_3$ was added thereto. After refluxed at 100° C. for about 10 hours, the reaction mixture was worked up with water and hexane, and then purified by silica gel column chromatography to obtain the triphenyl compound with a yield of 93%. Then, 3.7 g of the triphenyl compound was dissolved into 20 ml of dry THF and 5 ml of 2.0M LDA was added slowly dropwise thereto at −78° C. After an anion was formed over about 3 hours, 1.19 g of trimethylsilyl chloride was added to the anion at low temperature and the reaction mixture was warmed to room temperature. After stirred at room temperature for about 1 hour, the reaction mixture was worked up with water and hexane, and then recrystallized from hexane/MeOH solvent to obtain the silicon-containing compound represented by the above formula (yield: 92%). 400 MHz $^1$H-NMR, CDCl$_3$, δ (ppm): 0.42 (s, 9H), 0.85~0.94 (m, 3H), 1.33~1.41 (m, 4H), 1.62~1.70 (m, 2H), 2.67 (t, 2H), 6.99 (d, 2H), 7.22 (d, 2H), 7.29 (d, 2H), 7.51 (d, 2H).

Example 15

Liquid Crystal Composition (1)

A liquid crystal composition was prepared from the materials as shown in the following Table 1. In Table 1, each percent ratio refers to parts by weight per hundred parts of composition.

TABLE 1

| COMPOUND AND CONTENT | |
|---|---|
| (structure) | 15% |
| (structure) | 15% |
| (structure) | 14% |
| (structure) | 14% |

TABLE 1-continued
COMPOUND AND CONTENT
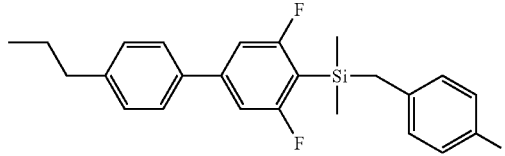 10%
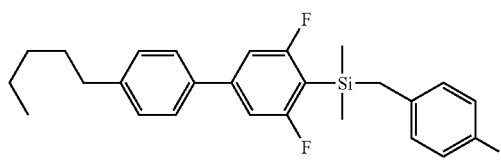 10%
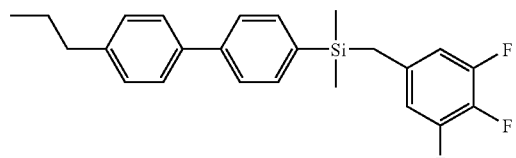 6%
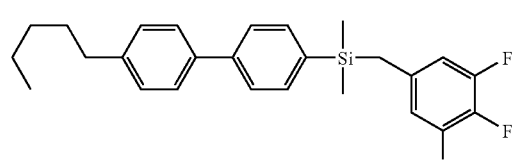 6%
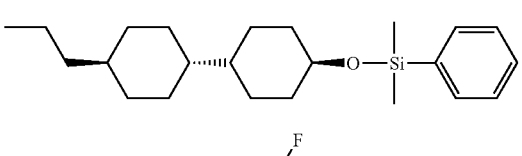 6%
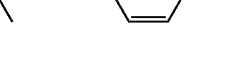 4%
Example 16
Liquid Crystal Composition (2)
A liquid crystal composition was prepared from the materials as shown in the following Table 2. In Table 2, each percent ratio refers to parts by weight per hundred parts of composition.
TABLE 2
COMPOUND AND CONTENT
 20%
TABLE 2-continued
COMPOUND AND CONTENT
 20%
 15%
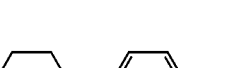 15%
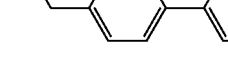 10%
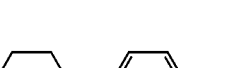 10%
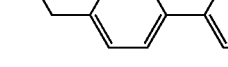 4%
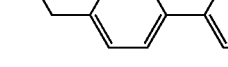 3%
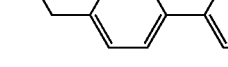 3%

Example 17

Liquid Crystal Composition (3)

A liquid crystal composition was prepared from the materials as shown in the following Table 3. In Table 3, each percent ratio refers to parts by weight per hundred parts of composition.

TABLE 3

| COMPOUND AND CONTENT | |
|---|---|
| [structure] | 15% |
| [structure] | 15% |
| [structure] | 11% |
| [structure] | 11% |
| [structure] | 10% |
| [structure] | 10% |
| [structure] | 6% |

TABLE 3-continued

| COMPOUND AND CONTENT | |
|---|---|
| [structure] | 6% |
| [structure] | 5% |
| [structure] | 5% |
| [structure] | 3% |
| [structure] | 3% |

Experimental Example 1

Evaluation for Physical Properties of Liquid Crystal Composition

The liquid crystal compositions according to the present invention were evaluated for their physical properties according to the following test.

The liquid crystal compositions according to Examples 15~17 were used. Each composition was introduced into a test tube in an amount of 1 g under the nitrogen atmosphere, and then heated at 150° C. for 2 hours to measure the phase transition temperature. Herein, clearing point (c.p.) of each composition refers to the isotropic liquid phase transition temperature in a nematic phase. Additionally, optical anisotropy ($\Delta n$) of each composition was measured at 20° C./589 nm, while dielectric anisotropy ($\Delta \epsilon$) of each composition was measured at 20° C./1 kHz. Also, viscosity of each composition was measured at 20° C. The results are shown in the following Table 4.

After the test, it can be seen that the liquid crystal compositions according to Examples 15~17 that comprise, as an active component, the novel silicon-containing compound represented by formula 1 according to the present invention, show high positive (+) dielectric anisotropy and low viscosity (see Table 4).

TABLE 4

| Ex. | Clearing point (° C.) | Optical anisotropy | Dielectric anisotropy | Viscosity (mPas) |
|---|---|---|---|---|
| 15 | 88 | 0.107 | 11.1 | 118 |
| 16 | 85 | 0.089 | 10.2 | 95 |
| 17 | 97 | 0.115 | 11.9 | 124 |

INDUSTRIAL APPLICABILITY

As can be seen from the foregoing, the present invention provides a novel nematic liquid crystal compound, which has low viscosity and high positive dielectric anisotropy, and a liquid crystal composition comprising the same compound. According to the present invention, it is possible to provide a liquid crystal display device that satisfies various desired characteristics, including a fast response time and a low driving voltage.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

wherein A is selected from the group consisting of $SiMe_2O_{k1}(CQ_2)_{n1}$, $SiEt_2O_{k1}(CQ_2)_{n1}$, $SiF_2O_{k1}(CQ_2)_{n1}$, $SiCl_2O_{k1}(CQ_2)_{n1}$, $SiMe_2(CQ_2)_{n1}O_{k1}$, $SiEt_2(CQ_2)_{n1}O_{k1}$, $SiF_2(CQ_2)_{n1}O_{k1}$, $SiCl_2(CQ_2)_{n1}O_{k1}$, $O_{k1}SiMe_2(CQ_2)_{n1}$, $O_{k1}SiEt_2(CQ_2)_{n1}$, $O_{k1}SiF_2(CQ_2)_{n1}$, $O_{k1}SiCl_2(CQ_2)_{n1}$, $(CQ_2)_{n1}O_{k1}SiMe_2$, $(CQ_2)_{n1}O_{k1}SiEt_2$, $(CQ_2)_{n1}O_{k1}SiF_2$, $(CQ_2)_{n1}O_{k1}SiCl_2$, $O_{k1}(CQ_2)_{n1}SiMe_2$, $O_{k1}(CQ_2)_{n1}SiEt_2$, $O_{k1}(CQ_2)_{n1}SiF_2$, $O_{k1}(CQ_2)_{n1}SiCl_2$, $(CQ_2)_{n1}SiMe_2O_{k1}$, $(CQ_2)_{n1}SiEt_2O_{k1}$, $(CQ_2)_{n1}SiF_2O_{k1}$, $(CQ_2)_{n1}SiCl_2O_{k1}$, $(CH_2)_{n1}$, $CH=CH$, $C \equiv C$, O, S, COO, OCO, $CF_2O$, $OCF_2$, OCOO, $CH_2O$, $CH_2CO$, $OCH_2$ and $COCH_2$, wherein $k_1$ is 0 or 1, Q is H or F, $n_1$ is an integer between 0 and 3;

M is C, N or Si, with the proviso that if M is N, $L_3$ or $L_7$ is null;

Z is C;

each of $a_1$, $a_2$ and $a_3$ is independently selected from C, NR and O;

E is selected from the group consisting of $SiMe_2O_{k2}(CQ_2)_{n2}$, $SiEt_2O_{k2}(CQ_2)_{n2}$, $SiF_2O_{k2}(CQ_2)_{n2}$, $SiCl_2O_{k2}(CQ_2)_{n2}$, $SiMe_2(CQ_2)_{n2}O_{k2}$, $SiEt_2(CQ_2)_{n2}O_{k2}$, $SiF_2(CQ_2)_{n2}O_{k2}$, $SiCl_2(CQ_2)_{n2}O_{k2}$, $O_{k2}SiMe_2(CQ_2)_{n2}$, $O_{k2}SiEt_2(CQ_2)_{n2}$, $O_{k2}SiF_2(CQ_2)_{n2}$, $O_{k2}SiCl_2(CQ_2)_{n2}$, $(CQ_2)_{n2}O_{k2}SiMe_2$, $(CQ_2)_{n2}O_{k2}SiEt_2$, $(CQ_2)_{n2}O_{k2}SiF_2$,

The invention claimed is:

1. A silicon-containing compound represented by the following formula 1:

[Formula 1]

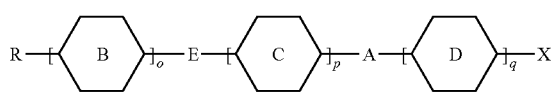

(I)

wherein A is selected from the group consisting of $SiMe_2(CQ_2)_{n1}$, Q is H or F, $n_1$ is an integer between 0 and 2;

ring B is selected from the group consisting of

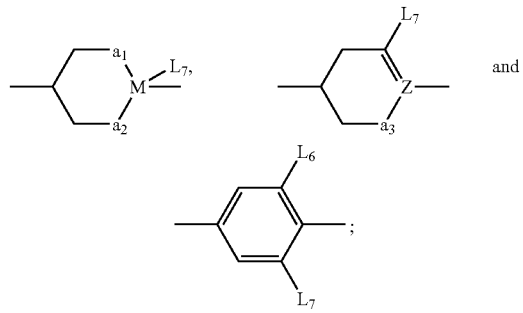

ring C is selected from the group consisting of

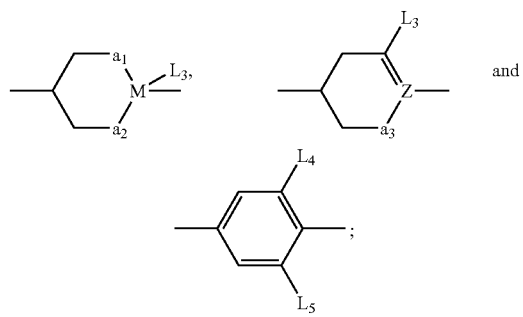

ring D is selected from the group consisting of

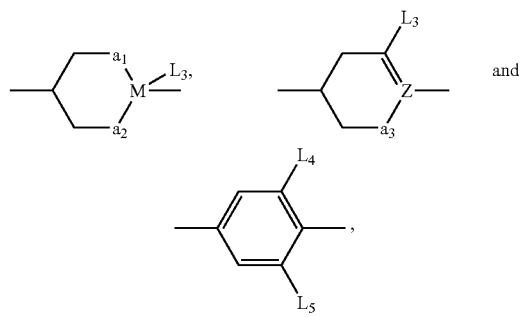

at least one of ring B, ring C and ring D contains

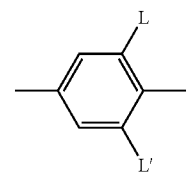

and each of L and L' is independently selected from the group consisting of halogen atoms, CN, $CF_3$, $OCF_3$ and NCS;

wherein the substituents, which are introduced into ring B, ring C or ring D and represented by $L_1$ to $L_7$, are independent from each other, even if they have the same designations;

M is selected from C, N and Si, with the proviso that if M is N, $L_3$ or $L_7$ is null;

Z is C;

each of $a_1$, $a_2$ and $a_3$ is independently selected from C, NR and O;

E is selected from the group consisting of $SiMe_2(CQ_2)_{n2}$, $SiEt_2(CQ_2)_{n2}$, $SiF_2(CQ_2)_{n2}$, $SiCl_2(CQ_2)_{n2}$, $SiMe_2(CQ_2)_{n2}O_{k2}$, $SiEt_2(CQ_2)_{n2}O_{k2}$, $SiF_2(CQ_2)_{n2}O_{k2}$, $SiCl_2(CQ_2)_{n2}Ok_2$, $O_{k2}SiMe_2(CQ_2)_{n2}$, $O_{k2}SiEt_2(CQ_2)_{n2}$, $O_{k2}SiF_2(CQ_2)_{n2}$, $O_{k2}SiCl_2(CQ_2)_{n2}$, $(CQ_2)_{n2}O_{k2}SiMe_2$, $(CQ_2)_{n2}O_{k2}SiEt_2$, $(CQ_2)_{n2}O_{k2}SiF_2$, $(CQ_2)_{n2}O_{k2}SiCl_2$, $O_{k2}(CQ_2)_{n2}SiMe_2$, $O_{k2}(CQ_2)_{n2}SiEt_2$, $O_{k2}(CQ_2)_{n2}SiF_2$, $O_{k2}(CQ_2)_{n2}SiCl_2$, $(CH_2)_{n2}$, $C{\equiv}C$, COO, OCO, $CF_2O$, $OCF_2$, OCOO, $CH_2O$, $CH_2CO$, $OCH_2$ and $COCH_2$, wherein $k_2$ is 0 or 1, Q is H or F, and $n_2$ is an integer between 0 and 2;

R is selected from the group consisting of H, a $C_1$~$C_{15}$ alkyl group and a $C_2$~$C_{15}$ alkene group, wherein the alkene group is $CH{=}CH_2$, $CH{=}CHCH_3$ (E,Z), $CH_2CH{=}CH_2$, $CH{=}CHCH_2CH_3$ (E,Z), $CH_2CH{=}CHCH_3$ (E,Z), $CH_2CH_2CH{=}CH_2$, $CH{=}CHCH_2CH_2CH_3$ (E,Z), $CH_2CH{=}CHCH_2CH_3$ (E,Z), $CH_2CH_2CH{=}CHCH_3$ (E,Z) or $CH_2CH_2CH_2CH{=}CH_2$;

$R_1$ is selected from the group consisting of H, a $C_1$~$C_{15}$ alkyl group and a $C_2$~$C_{15}$ alkene group, wherein the alkene group is $CH{=}CH_2$, $CH{=}CHCH_3$ (E,Z), $CH_2CH{=}CH_2$, $CH{=}CHCH_2CH_3$ (E,Z), $CH_2CH{=}CHCH_3$ (E,Z), $CH_2CH_2CH{=}CH_2$, $CH{=}CHCH_2CH_2CH_3$ (E,Z), $CH_2CH{=}CHCH_2CH_3$ (E,Z), $CH_2CH_2CH{=}CHCH_3$ (E,Z) or $CH_2CH_2CH_2CH{=}CH_2$;

X is selected from the group consisting of H, $SiR_2R_3R_4$, $CF_3$, $OCF_3$, CN, NCS, halogen atoms, R and alkoxy group ($OR_1$);

each of $R_2$, $R_3$ and $R_4$ is independently selected from R and halogen atoms;

each of $L_1$, $L_2$, $L_3$, $L_4$, $L_5$, $L_6$ and $L_7$ is independently selected from the group consisting of H, halogen atoms, CN, $CF_3$, $OCF_3$ and NCS;

each of o, p and q independently represents an integer between 1 and 2; and at least one of E, A and X contains silicon.

2. The silicon-containing compound according to claim 1, which has zero (0) or positive dielectric anisotropy.

3. The silicon-containing compound according to claim 1, which is a compound represented by any one formula selected from the group consisting of formula 2~formula 10:

[Formula 2]

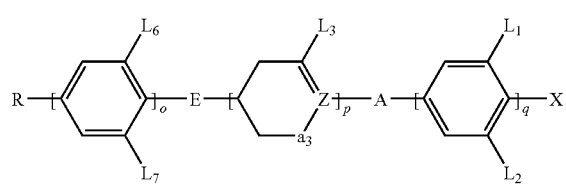

(II)

[Formula 3]

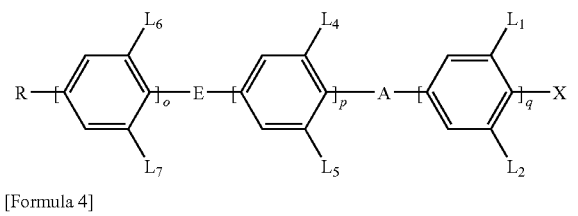

(III)

[Formula 4]

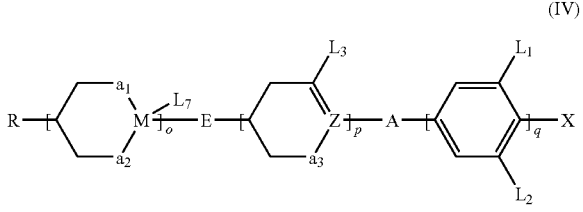

(IV)

[Formula 5]

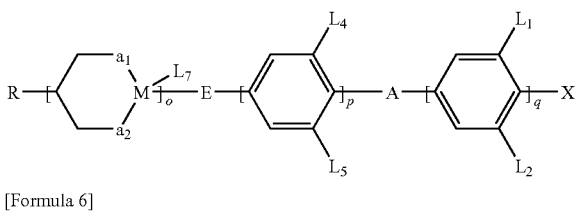

(V)

[Formula 6]

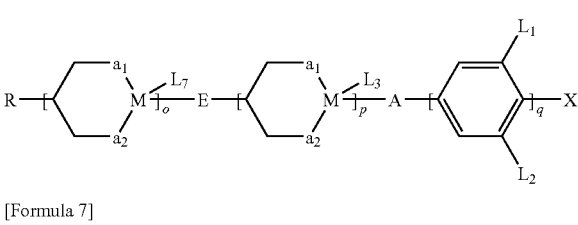

(VI)

[Formula 7]

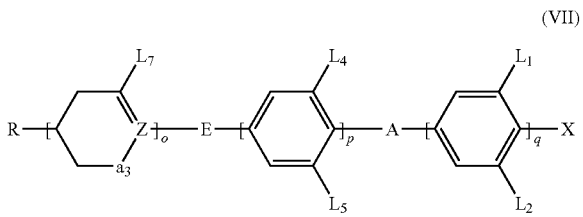

(VII)

[Formula 8]

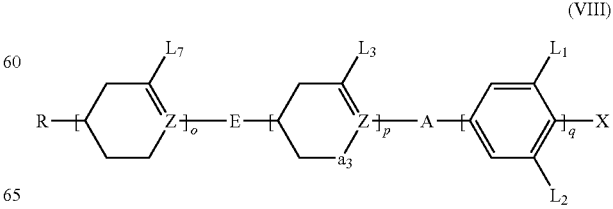

(VIII)

-continued

[Formula 9]

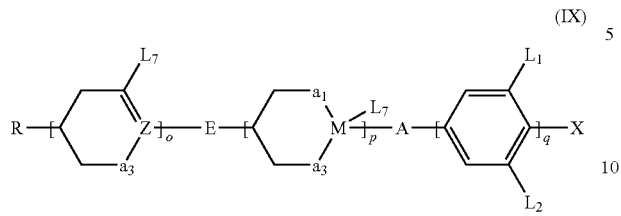

(IX)

[Formula 10]

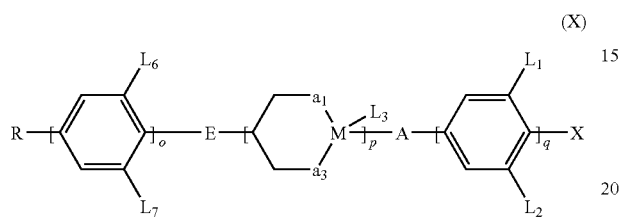

(X)

wherein A is selected from the group consisting of SiMe$_2$ (CQ$_2$)$_{n1}$, Q is H or F, n$_1$ is an integer between 0 and 2;

M is C, N or Si, with the proviso that if M is N, L$_3$ or L$_7$ is null;

Z is C;

each of a$_1$, a$_2$ and a$_3$ is independently selected from C, NR and O;

E is selected from the group consisting of SiMe$_2$(CQ$_2$)$_{n2}$, SiEt$_2$(CQ$_2$)$_{n2}$, SiF$_2$(CQ$_2$)$_{n2}$, SiCl$_2$(CQ$_2$)$_{n2}$, SiMe$_2$(CQ$_2$)$_{n2}$O$_{k2}$, SiEt$_2$(CQ$_2$)$_{n2}$O$_{k2}$, SiF$_2$(CQ$_2$)$_{n2}$O$_{k2}$, SiCl$_2$(CQ$_2$)$_{n2}$O$_{k2}$, (CQ$_2$)$_{n2}$SiEt$_2$, (CQ$_2$)$_{n2}$SiF$_2$, (CQ$_2$)$_{n2}$SiCl$_2$, O$_{k2}$(CQ$_2$)$_{n2}$SiMe$_2$, O$_{k2}$(CQ$_2$)$_{n2}$SiEt$_2$, O$_{k2}$(CQ$_2$)$_{n2}$SiF$_2$, O$_{k2}$(CQ$_2$)$_{n2}$SiCl$_2$, (CH$_2$)$_{n2}$, C≡C, O, S, COO, OCO, CF$_2$O, OCF$_2$, OCOO, CH$_2$O, CH$_2$CO, OCH$_2$ and COCH$_2$, wherein k$_2$ is 0 or 1, Q is H or F, and n$_2$ is an integer between 0 and 2;

R is selected from the group consisting of H, a C$_1$~C$_{15}$ alkyl group, and a C$_2$~C$_{15}$ alkene group, wherein the alkene group is CH═CH$_2$, CH═CHCH$_3$ (E,Z), CH$_2$CH═CH$_2$, CH═CHCH$_2$CH$_3$ (E,Z), CH$_2$CH═CHCH$_3$ (E,Z), CH$_2$CH$_2$CH═CH$_2$, CH═CHCH$_2$CH$_2$CH$_3$ (E,Z), CH$_2$CH═CHCH$_2$CH$_3$ (E,Z), CH$_2$CH$_2$CH═CHCH$_3$ (E,Z) or CH$_2$CH$_2$CH$_2$CH═CH$_2$;

R$_1$ is selected from the group consisting of H, a C$_1$~C$_{15}$ alkyl group and a C$_2$~C$_{15}$ alkene group, wherein the alkene group is CH═CH$_2$, CH═CHCH$_3$ (E,Z), CH$_2$CH═CH$_2$, CH═CHCH$_2$CH$_3$ (E,Z), CH$_2$CH═CHCH$_3$ (E,Z), CH$_2$CH$_2$CH═CH$_2$, CH═CHCH$_2$CH$_2$CH$_3$ (E,Z), CH$_2$CH═CHCH$_2$CH$_3$ (E,Z), CH$_2$CH$_2$CH═CHCH$_3$ (E,Z) or CH$_2$CH$_2$CH$_2$CH═CH$_2$;

X is selected from the group consisting of H, SiR$_2$R$_3$R$_4$, CF$_3$, OCF$_3$, CN, NCS, halogen atoms, and R and alkoxy group (OR$_1$);

each of R$_2$, R$_3$ and R$_4$ is independently selected from R and halogen atoms;

each of L$_1$, L$_2$, L$_3$, L$_4$, L$_5$, L$_6$ and L$_7$ is independently selected from the group consisting of H, halogen atoms, CN, CF$_3$, OCF$_3$ and NCS; and each of o, p and q independently represents an integer between 0 and 2 and wherein o+p+q>1.

4. The silicon-containing compound according to claim 1, which is selected from the group consisting of the following compounds:

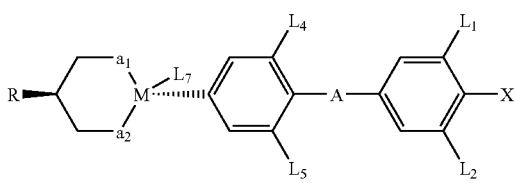

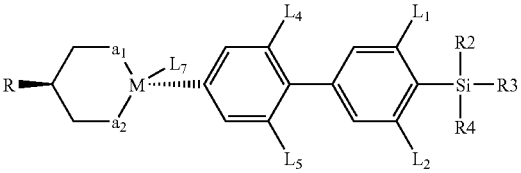

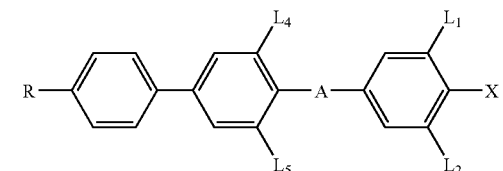

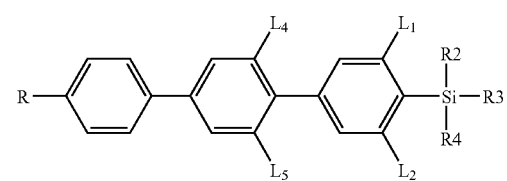

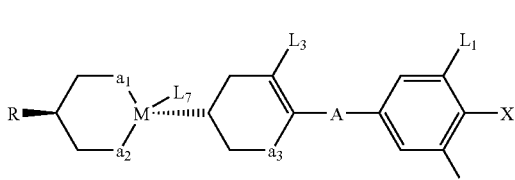

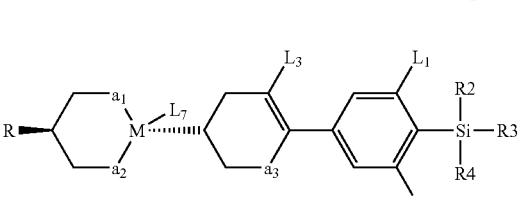

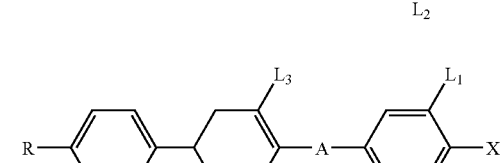

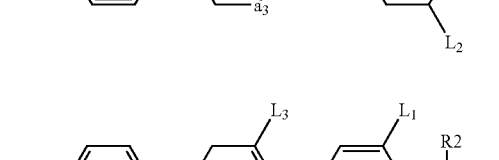

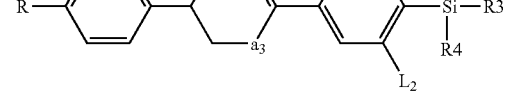

-continued

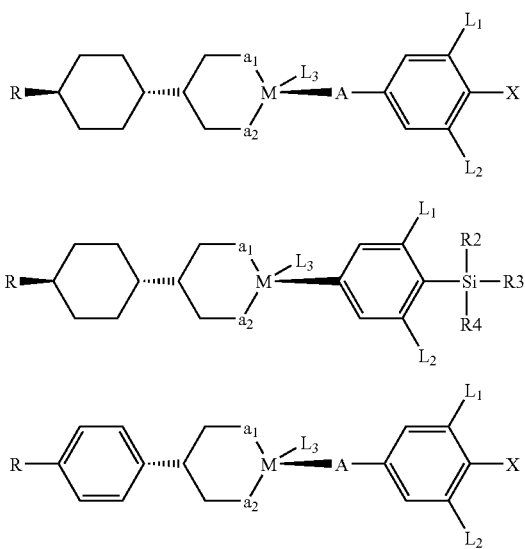

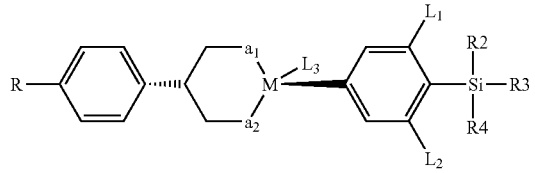

wherein A is selected from the group consisting of $SiMe_2(CQ_2)_{n1}$, and wherein, Q is H or F, $n_1$ is an integer between 0 and 2; and $R_1, R_2, R_3, R_4, M, a_1, a_2, a_3, L_1, L_2, L_3, L_4, L_5, L_7$ and X are the same as defined in claim 1.

5. The silicon-containing compound as claimed in claim 1, which has stereoisomers.

6. The silicon-containing compound as claimed in claim 5, wherein the stereoisomers of the silicon-containing compound are present in a ratio of trans-isomer:cis-isomer of 85~100:15~0.

* * * * *